(12) United States Patent
McGrew (10) Patent No.: US 6,930,779 B2
(45) Date of Patent: Aug. 16, 2005

(54) QUANTUM RESONANCE ANALYTICAL INSTRUMENT

(76) Inventor: Stephen P. McGrew, 9715 W. Sunset Hwy., Spokane, WA (US) 99224

( * ) Notice: Subject to any disclaimer, the term of this patent is extended or adjusted under 35 U.S.C. 154(b) by 384 days.

(21) Appl. No.: 10/286,338

(22) Filed: Nov. 1, 2002

(65) Prior Publication Data

US 2003/0123051 A1 Jul. 3, 2003

Related U.S. Application Data (60) Provisional application No. 60/338,506, filed on Nov. 6, 2001.

(51) Int. Cl.[7] ................................. G01B 9/02
(52) U.S. Cl. .................. 356/450; 356/491; 356/451
(58) Field of Search ...................... 356/450, 491, 356/451

(56) References Cited

U.S. PATENT DOCUMENTS

| | | | | |
|---|---|---|---|---|
| 5,530,544 A | * | 6/1996 | Trebino et al. | 356/450 |
| 5,541,947 A | * | 7/1996 | Mourou et al. | 372/25 |
| 5,589,936 A | * | 12/1996 | Uchikawa et al. | 356/450 |
| 6,201,916 B1 | * | 3/2001 | Eggleton et al. | 385/122 |
| 6,219,142 B1 | * | 4/2001 | Kane | 356/450 |
| 6,456,380 B1 | * | 9/2002 | Naganuma | 356/450 |
| 2004/0128081 A1 | * | 7/2004 | Rabitz et al. | 702/23 |

* cited by examiner

Primary Examiner—Gregory J. Toatley, Jr.
Assistant Examiner—Patrick Connolly
(74) Attorney, Agent, or Firm—Dorsey & Whitney LLP (57) ABSTRACT

Quantum based systems for detecting materials in a sample, including biological, chemical and physical materials are described. The systems are based on exciting the sample containing the material with a femtosecond to nanosecond probe pulse of collimated light, which is tailored to optimize detection of a given material by separating the probe pulse into component features of frequency, polarization, phase and/or amplitude. The component features are independently shaped and formed into a composite pulse selected to optimize a signature response pulse received from the material. Selection of the appropriate shapes for the component features of the pulse for a given material is accomplished by testing variations in the features on the material, assigning a fitness value to variants that tend to optimize a distinctive spectral response from the material, and using a genetic algorithm to select the combination of component features that enhances the distinctiveness of the response received over a typical background.

12 Claims, 6 Drawing Sheets

ORIGINAL PULSE          SHAPED PULSE

QUANTUM RESONANCE ANALYTICAL INSTRUMENT

CROSS-REFERENCE TO RELATED APPLICATIONS

This application claims priority to U.S. provisional patent application No. 60/338,506 entitled "Anthrax Detector" filed Nov. 6, 2001.

TECHNICAL FIELD

The invention relates to methods and devices for detecting materials in a sample by separating a coherent radiation pulse directed onto the sample into a plurality of pulses of different polarization sates, modulating the amplitude or phases of the plurality of separate pulses and coherently recombining the seprate pulses into a composite pulse having component features selected by a genetic algorithm to distinguish the spectral responses of the materials in the sample.

BACKGROUND OF THE INVENTION

Prior art includes a large body of published work relating to the shaping of femtosecond pulses and the interactions between various materials or molecules with the shaped pulses. It has been observed that in nonlinear systems such as molecules and semiconductor materials, intense light pulses of certain shapes can be used to enhance the fluorescent emission at particular wavelengths. The specific pulse shape depends on the complex energy band structure of the molecules or materials being studied. In principle, a detailed and precise understanding of the physics involved should be enough to calculate the optimal pulse shape, but in practice our understanding is insufficient and our computational tools are too crude to do the calculations.

Figure 1:
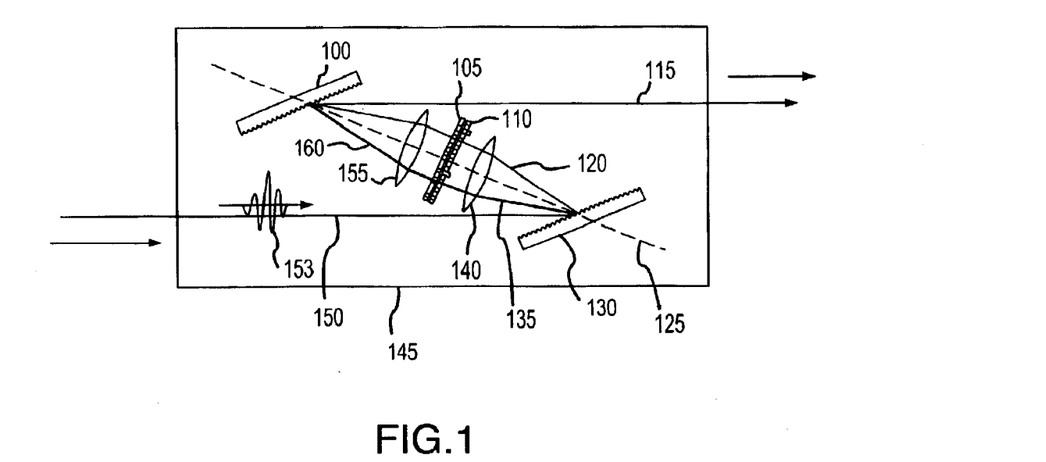
FIG. 1 illustrates a pulse shaper using a combination of prior art methods for shaping femtosecond light pulses adaptively.
Figure 2:
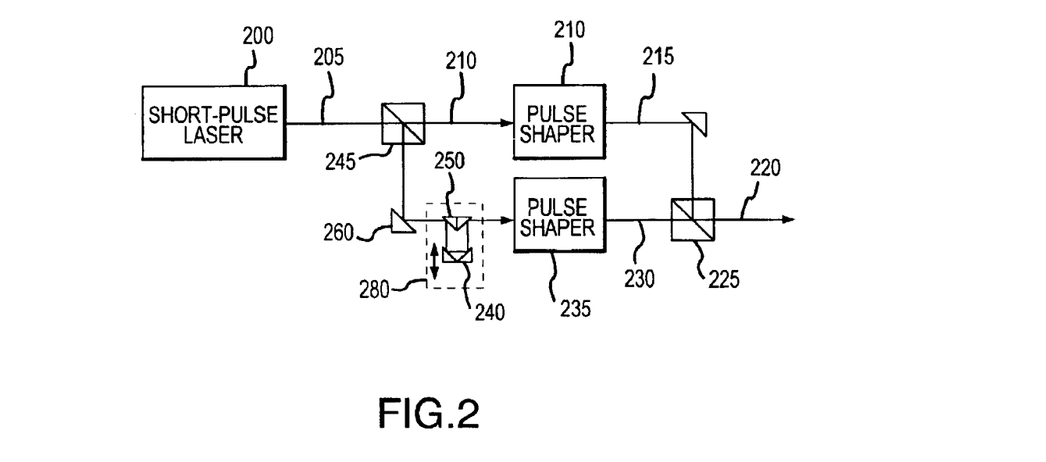
FIG. 2 illustrates an apparatus for shaping femtosecond light pulses adaptively with independent control of polarization, amplitude and phase at multiple wavelengths. The apparatus uses a pair of pulse shapers, one for each of two orthogonal polarization states in separate paths. A variable delay element is included in one of the paths to adjust the relative timing and/or phase of the two polarization states.

In "Feedback quantum control of population transfer using shaped femtosecond pulses", published in *Ultrafast Phenomena XI*, 1998, K. R. Wilson and his associates demonstrated a method for evolving an optimal pulse shape to control the quantum state of a complex molecular system. The method is illustrated in FIG. 1. A very brief light pulse is spread into a spectrum by a diffraction grating, then the spectrum is passed through a spatial light modulator which modulates each spectral component independently. The modulator can operate on phase, amplitude or both. Typical spatial light modulators used for pulse shaping are acousto-optic modulators, liquid crystal modulators and deformable-mirror arrays. The pulse is then reconstituted by focusing the modulated spectral components back to a point on a diffraction grating, which combines the components coherently into a single pulse. In essence, the spatial light modulator acts on the temporal Fourier transform of the initial pulse to re-form it in any way desired.

A substance such as a particular protein responds nonlinearly to a pulse of light. For example, an ultraviolet light pulse a few tens of femtoseconds long will induce fluorescence in most substances, and the spectrum of the fluorescence depends on the intensity of the pulse. If the intensity is great enough, there is an increased probability of multiphoton absorption resulting in electrons being elevated to energy levels higher than the energy of a single photon, which leads to emission at wavelengths that single-photon absorption cannot produce.

In addition to intensity, the spectral content of a light pulse and the relative phase and polarization of the spectral components can affect strongly the response of an illuminated sample. For example, it has been shown by Bardeen et al (Ref. 1) that when a laser light pulse is shaped appropriately, the intensity of a fluorescence from an irradiated sample can be much higher than it is with an arbitrarily shaped pulse. That is, the ratio of the intensity of a specific emission line to the intensity of another specific emission line can be maximized by using an optimally-shaped pulse.

The importance of pulse shape to the response of a nonlinear system like an atom can be understood by considering a double pendulum stimulated by a short series of impacts. If a series of impacts strike the pendulum at times separated by a time equal to the period of the fundamental mode of the pendulum, the pendulum will respond by swinging without wiggling. If, however, the impacts are timed so that some are synchronous with the fundamental mode, but other impacts are interspersed with the first impacts so that the other impacts are synchronous with the vibrational period of the upper mass, the pendulum will respond by both swinging and wiggling. In the case of a quantum mechanical system like a molecule, a properly shaped pulse can elevate electrons to a specific energy level and then give them a second "kick" to elevate them further to another energy level that is otherwise not easily accessible. Decay from that energy level to other energy levels en route to the ground state, then, produces emission lines that will only be present when the excitation pulse has precisely the shape required to provide the first "kick" followed by a properly timed second "kick". Furthermore, the direction of the electric fields in a pulse during the first and second "kicks" is important because the vibratory state or quantum state of an electron in a molecule or atom has a directional component. So, in an optimal pulse, the polarization state of the light may need to change once or even several times within the pulse duration.

In the prior art, femtosecond laser pulses have been shaped by forming their temporal Fourier transform, manipulating individual Fourier components independently in both phase and amplitude, and then forming the inverse Fourier transform. This is accomplished as illustrated in FIG. 1, by forming the dispersed spectrum of an original pulse 153 using a diffraction grating 130, passing the spread spectrum through a spatial light modulator 105, 110 (such as a liquid crystal light valve or an acousto-optic light modulator) to selectively attenuate and/or delay various portions of the spectrum, and then focusing the spectrum back together onto a second diffraction grating 100, where the pulse is re-formed into a modified shape.

Also in the prior art, the optimum pulse shape is determined empirically by monitoring the emission spectrum of a sample irradiated by the shaped pulse and adjusting the shape until the emission spectrum is optimized. For example, if the spatial light modulator 105, 110 is a liquid crystal light modulator, the pixels of the modulator can be treated as "genes" while the height of a specific emission line can be treated as "fitness" in a genetic algorithm.

The basic techniques of laser pulse shaping and pulse shape optimization have been explored by many researchers, with the purpose of performing measurements on molecular dynamics, generating x-rays, and controlling chemical reactions.

SUMMARY OF THE INVENTION

Disclosed herein are an apparatus and method for recognizing specific molecules, complexes or other substances or structures by subjecting a sample to a query pulse and detecting a response pulse. The query pulse is tailored to the specific substance or structure, and the response pulse in response to the query pulse is unique to the substance or structure being sought. X-ray, UV, visible, IR, terahertz, RF, or acoustic pulses are used as appropriate for the substance or structure being sought. The response pulse may be X-ray, UV, visible, IR, terahertz, RF, or acoustic; and is not necessarily the same type as the query pulse. A unique feature of the present invention is the use of query pulses tailored in the amplitude and phase of spectral content in order to stimulate optimally a specific response that is specific to the substance or structure being sought.

BRIEF DESCRIPTION OF THE INVENTION

The present invention employs shaped pulses to recognize specific substances and structures. Whereas prior art has used shaped pulses to study the quantum dynamics of specific molecules, there is no prior art in which shaped pulses have been used to recognize, identify or detect specific molecules or substances.

According to the present invention, a short coherent pulse of radiation is shaped by selectively attenuating and/or delaying various spectral and/or polarization components of an original pulse. The shaped pulse is focused onto a substance. The pulse interacts nonlinearly with the substance to produce a characteristic response, if the pulse shape is precisely tailored to the structure of the substance. Other substances with different structures do not produce the same response to pulses of that particular shape. When the characteristic response is received from a sample irradiated with that particular pulse shape, it is known with very high confidence that the sample contains the corresponding substance.

Figure 5:
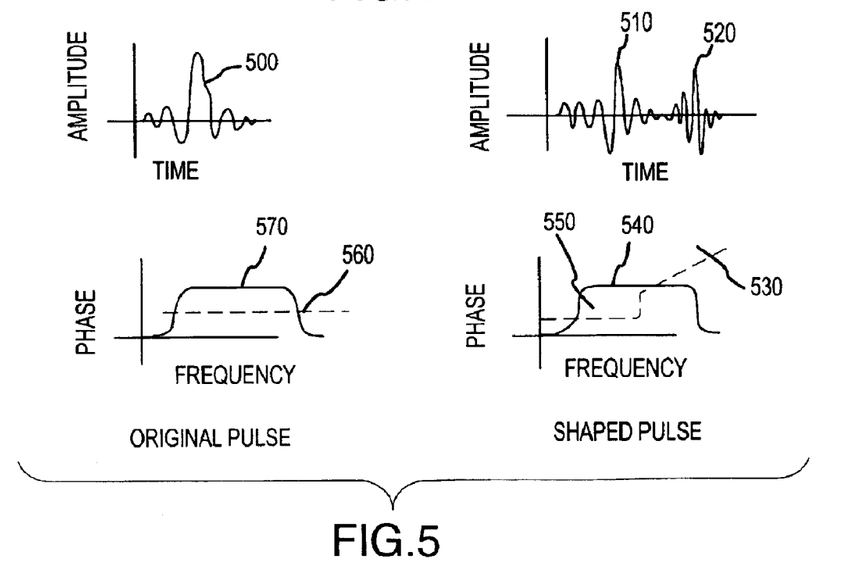
FIG. 5 illustrates various representations of an optical pulse before and after pulse shaping in phase and amplitude only.

As described in prior art publications and illustrated in FIG. 5 (original pulse), a femtosecond laser pulse contains a broad continuum of light frequencies. The pulse may be spectrally dispersed by focusing it to a narrow beam and reflecting it from a diffraction grating as illustrated in FIG. 1. As shown in FIG. 1, the spread spectrum is then passed through a spatial light modulator such as an acousto-optic modulator or a liquid crystal TV screen, or it may be reflected from a deformable-membrane spatial light modulator. The spatial light modulator selectively delays and/or attenuates the various spectral components of the pulse. The spectrum emerging from the modulator is then refocused to a point and reflected again from a diffraction grating to re-form the pulse. The re-formed pulse has a new shape depending on the details of the modulation performed on the various spectral components. FIG. 5 illustrates an original pulse 500 re-shaped into a new pulse that has a low-frequency component 510 that is slightly delayed relative to a higher-frequency component 520. The re-shaping in this case is accomplished by spreading the original pulse into a spectrum 570, then delaying the phase of the lower-frequency components 500 of the spectrum. Note that in the case illustrated in FIG. 5, the relative phase delay is proportional to the frequency, but in general any phase delay versus frequency relationship may be used.

In the present methods, the shaped pulse is used to excite fluorescence from a known substance, and an optimization procedure is followed to discover a particular modulation function that maximally enhances a distinctive spectral feature in the fluorescence spectrum emitted by the substance. For example, a single emission line having relatively low intensity in the ordinary fluorescence spectrum might be enhanced by one or more orders of magnitude by an excitation pulse having an optimal shape. Alternatively, one emission line or other feature that is ordinarily in the fluorescence spectrum might be greatly decreased when the excitation pulse has a specific shape, or, features in the absorption spectrum may be enhanced or diminished by exciting the substance with an optimal pulse. The spectral features of interest may be measured at the time of the excitatory pulse, or at any time thereafter. The absorption spectrum and emission spectrum of a substance are dependent on the quantum state of a substance, and the quantum state typically changes very rapidly following initial excitation. Accordingly, it is advantageous to employ two or more pulses. The first pulse may be called a "pump" pulse, and subsequent pulses may be called a "probe" pulse.

Sometimes it is advantageous to illuminate the sample first with a long-duration coherent pulse up to several milliseconds long, to place most of the target molecules in the sample into a specific first quantum state. Then a second, brief shaped pulse may be used to move the target molecules from the first quantum state to a second quantum state; and finally a third, brief shaped pulse may be used to measure the number of molecules in the second quantum state via a measurement of the absorption spectrum or the emission spectrum. The relative timing and phase of the pump and probe pulses can affect the response of the molecules to the pulses dramatically.

It is not within the current capabilities of the art to predict exactly what pulse shape is needed to enhance or decrease a given feature of the fluorescence spectrum of a particular substance. However, a pulse-shaping system may be "trained" to generate a pulse shape that has the desired effect, as described by Bardeen et al (Ref. 1). If necessary, the pulse shape can then be calculated from the modulation applied to obtain the effective pulse, or the pulse shape can be measured directly.

Figure 3:
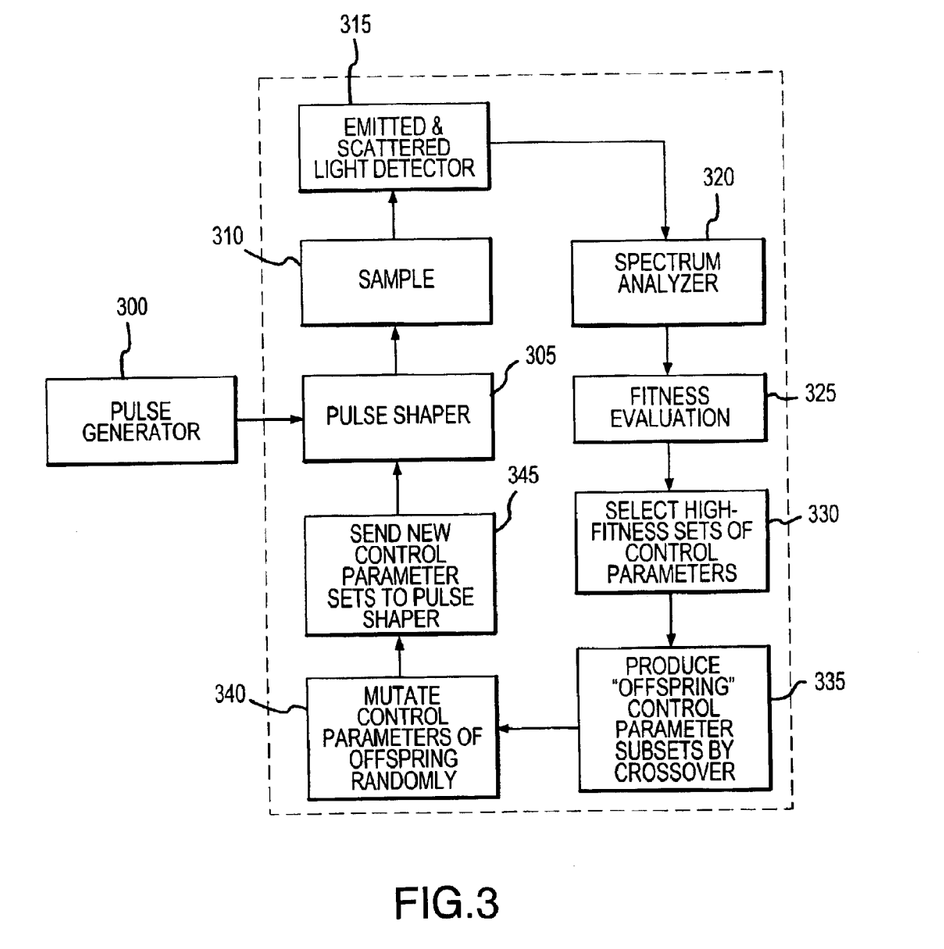
FIG. 3 is a diagram representing the training procedure for recognition of a specific substance

A procedure for carrying out the processes involved in this invention is diagrammed in FIG. 3. A light pulse generator 300 emits a stream of pulses of consistent shape and structure. A pulse shaper 305 adjusts the shape of the light pulse, which is conveyed to a sample 310. Emitted and scattered light is detected by detector 315, and its spectrum is analyzed by a spectrum analyzer 320. The "fitness" of the pulse shape is determined by a fitness evaluator 325. Fitness may be, for example, the inverse of the integral of the square of the difference between the normalized intensities of corresponding spectral components of the emission or absorption spectrum from the sample in response to an un-shaped pulse and the shaped pulse. In that case, the pulse shape is optimum when the fitness is maximized.

A "population" of different pulse shapes are generated by the pulse shaper, and the fitness of each pulse shape in the population is calculated. The high-fitness pulses (that is, the control parameter sets that determine the shapes of the pulses) are selected 330 to produce "offspring" sets of control parameters to determine new pulse shapes in a subsequent generation. The "offspring" may be constructed 335 by the evolutionary operators of recombination or mutation 340, or by a mixture of the two operations of a genetic algorithm. The offspring are sent 345 to the pulse shaper to complete the first cycle. A nearly optimum pulse shape is achieved after a series of such cycles.

If a particular spectral feature and an optimal pulse shape have been found for a given substance, then that pulse shape and the spectral feature together are unique to that substance. It is a primary objective of the methods disclosed herein to use an optimally shaped laser pulse as a probe to excite light emission from an unknown sample, and to determine the presence of an absence of a known substance in that sample by the presence or absence of the corresponding spectral feature in the emission.

Another purpose of the methods disclosed herein is to provide a new way to identify specific substances by observing their optical response to laser pulses whose shapes are tailored to produce a specific optical response in specific substances.

Another purpose of the methods disclosed herein is to provide a system that rapidly detects specific pathogens or chemical/biological warfare agents.

Another purpose of the methods disclosed herein is to identify documents, products or packages by detecting the relative quantities of specific substances.

Another purpose of the methods disclosed herein is to identify and measure the quantity of specific molecular species in fluids or gasses.

Another purpose of the methods disclosed herein is to provide a scanning near-field optical microscope capable of detecting and identifying specific molecular species or elements in a sample with nanometer-scale resolution.

Another purpose of the methods disclosed herein is to provide an apparatus for controlling the polarization as well as shape of an optical pulse during the time evolution of the pulse.

Another purpose of the methods disclosed herein is to provide a method for obtaining a unique "signature" for a molecular species.

Another purpose of the methods disclosed herein is to sort molecules, microbes, cells, spores and other particles by their optical properties.

Another purpose of the methods disclosed herein is to selectively kill specific microbial species in a sample by irradiating the sample with pulses that interact selectively with those species.

Another purpose of the methods disclosed herein is to extend the capabilities of NMR spectroscopy.

Another purpose of the methods disclosed herein is to provide a general method for excitation of specific vibrational modes in nonlinear structures by use of a shaped pulse of acoustic, optical, RF or other radiation.

Another purpose of the methods disclosed herein is to provide a method for driving a population of molecules into a predetermined quantum state, as opposed to driving only certain atoms in the molecules into a predetermined quantum state.

Beyond the purposes and objectives described above, the methods disclosed herein have useful applications in rapid screening of mail for pathogens, detection of pathogens in water, rapid counting and identification of fluorophore-tagged microbes, viruses and molecules, stimulation and control of specific chemical reactions, control of quantum states in nanometer-scale semiconductor "quantum dots", manipulating quantum states of molecules and quantum-mechanical structures for quantum computation, and optimizing any process involving the interaction of light with matter. When the pulsed radiation is x-rays rather than visible light, optimization of the shape of a pulse improves contrast of x-ray imaging by enhancing the absorption of x-rays by specific substances.

DETAILED DESCRIPTION

Embodiment #1: Apparatus and Method for Detecting Anthrax Spores

Figure 12:
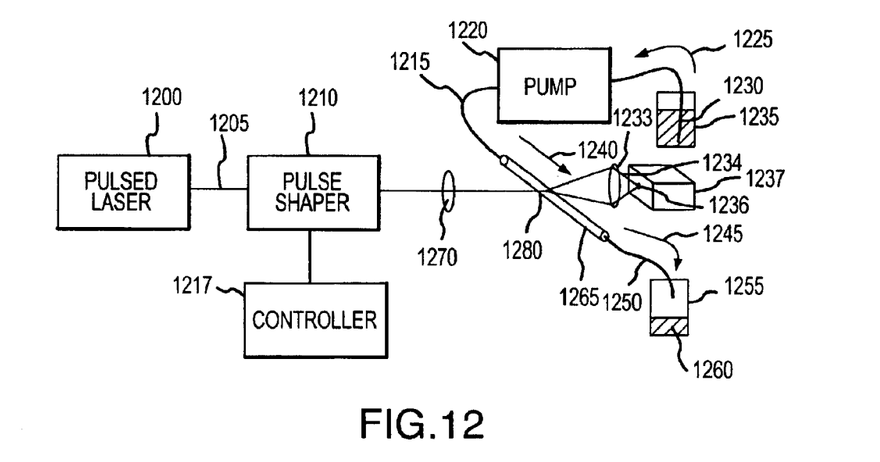
FIG. 12 illustrates an apparatus for selectively killing specific cells or spores via shaped optical pulses

The apparatus of FIG. 12 includes a source 1200 of femtosecond light pulses, a pulse shaper 1210, a fluorescence spectrometer 1237, optics 1270 to direct shaped light pulses to a sample of fluid in a sample holder 1265, means 1237 for analyzing the spectrum and polarization of light emitted by the sample in response to illumination by a light pulse, and means 1217 for controlling the pulse shaper 1210. In the example shown in FIG. 12, the sample holder is a transparent capillary tube 1265, a source reservoir 1230, the tubing 1215 and 1250, and the receiver reservoir 1255. However, the sample holder can be a microscope slide, a "gene array chip", a clamp, or any other device that can hold a sample for analysis. In fact, the sample holder can be the sample itself of part of the sample's environment, if, for example, the sample is a letter in a mail sorting facility, dust on a table surface, or microbes on the leaf of a tree.

This apparatus is "trained" to recognize a specific pathogen such as anthrax spores or smallpox viruses by first placing a sample of the pathogen in the sample holder, irradiating the pathogen by one or more light pulses, and selecting a feature from the fluorescence spectrum emitted by the pathogen in response to the pulses. The pulse shape is varied while the selected spectral feature is observed, and an optimization procedure is followed to find the pulse shape that maximally enhances the selected feature.

For example, control parameters of pulse shape (such as voltages controlling the attenuation and delay of spectral and polarization components of the pulse) may be treated as genes in a genetic algorithm, and the strength or contrast of the selected feature may be treated as fitness in the genetic algorithm to evolve a pulse shape that optimally enhances the selected feature. After optimization for a specific pathogen, the control parameters and the selected feature for that specific pathogen are stored in a computer memory.

In order to detect the specific pathogen in an unknown sample, the controller 1217 loads the optimal control parameters into the pulse shaper 1210 which then generates shaped pulses. Those shaped pulses stimulate fluorescent light emission 1234 by the sample. The fluorescence spectrum analyzer 1237 receives the fluorescent light from the sample and analyzes the fluorescent light to determine whether or not the selected feature is present, and its relative intensity. If the pathogen is present in the sample, the selected spectral feature will be detected. If the feature is not detected by the analyzer, either the pathogen is not present or it is present in too low a concentration to produce a detectable signal.

Embodiment #2: A Pulse Shaper with Phase, Amplitude and Polarization Control

Figure 7:
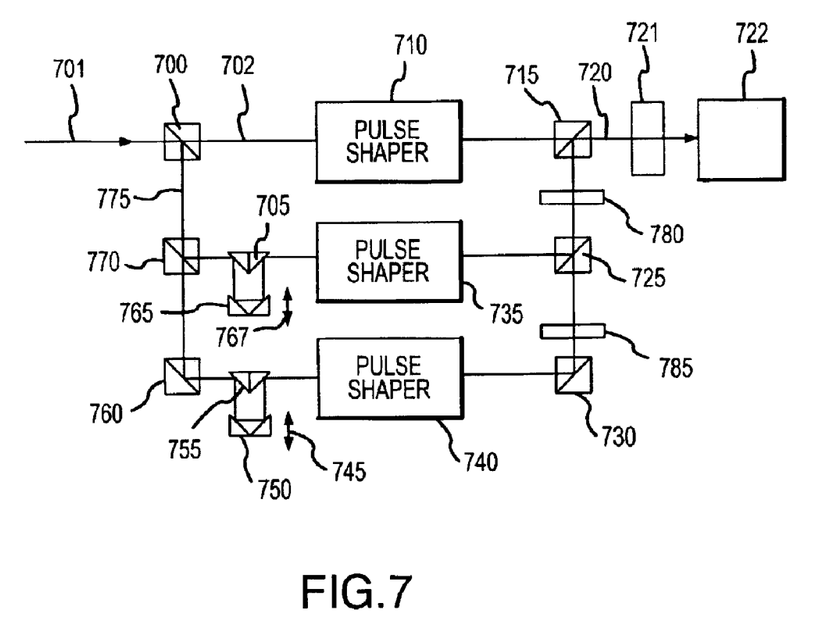
FIG. 7 illustrates a schematic of an apparatus for coherently summing multiple independently shaped pulses with variable delays between them.

The apparatus in FIG. 7 is a pulse shaper for light pulses, on the order of femtoseconds to nanoseconds in duration. An original collimated pulse 701 is split by a polarizing beamsplitter 700 into two pulses 775, 702 with orthogonal polarization. In the path of each pulse, a non-polarization pulse shaper 710, 735, 740 is placed. As shown in FIG. 1, in the non-polarization pulse shapers, a dispersive element 130 such as a diffraction grating or a prism spreads the spectrum of an original light pulse out to a line. The diverging light in the spread spectrum is collimated by a lens 140 or by a curved mirror, then is passed through one or more spatial light modulators 110,105 to adjust the relative phase and amplitude of each spectral component relative to the other components. After passing through the spatial light modulators, the light is focused to a point by a second lens 155 onto a second diffraction grating 100 where it is re-formed into a pulse having only one essentially pure polarization state.

Figure 6:
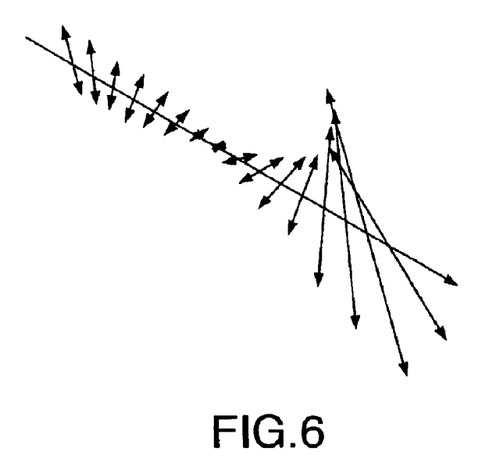
FIG. 6 is a representation of an optical pulse shaped in phase, amplitude and polarization.

As shown in FIG. 7, the pulses emerging from the two pulse shapers 710, 735, still having orthogonal polarizations, are recombined into a single collimated pulse by means of a polarizing beamsplitter 725. By using path length adjuster 765 to adjust the relative phase of the two orthogonal polarization components of each spectral component, any desirable polarization state (e.g., right circular, left circular, linear or elliptical) can be achieved for that component after the two polarization components are recombined. By thus adjusting the relative phase, amplitude and/or polarization state of every spectral component of the recombined pulse, any desired pulse shape can be generated as illustrated in FIG. 6. FIG. 6 illustrates a light pulse whose polarization direction rotates clockwise, then counterclockwise, as its amplitude varies.

Embodiment #3: Scanning Near-Field Optical Probe Microscope

Figure 4:
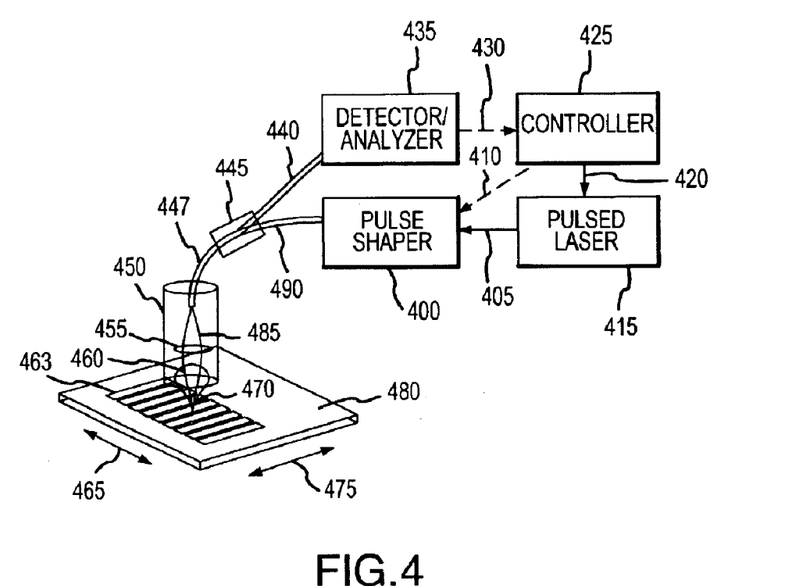
FIG. 4 illustrates a near-field optical scanning microscope using tailored optical pulses for specific substance recognition, including a pulsed laser, a pulse shaper feeding pulses into an optical fiber, a fiber beamsplitter, a near-field probe, and means for moving a sample relative to the probe.

As shown in FIG. 4, a shaped pulse of light may be coupled into an optical fiber 490 and thence into the optics 455, 460 of a near-field scanning optical probe microscope 450. Scattered light from the pulse and fluorescent light stimulated by the pulse may be gathered either by the optical fiber 447 or by other means such as a microscope objective and analyzed with respect to spectrum, polarization and phase by means of a spectrometer or time-resolved spectrometer and other suitable optics 435. Phase analysis requires interfering the gathered light with a portion of the original pulse and examining the position of fringes in the interference pattern. Scattered light may be analyzed for features in the absorption spectrum, while emitted fluorescent light may be analyzed for features in the emission spectrum. Any particular substance at the locus of the evanescent light field from the tip of the microscope probe will be coherently manipulated by a pulse optimally shaped for that substance, so that one or more features in its absorption spectrum or fluorescence spectrum is enhanced.

In order to determine a satisfactory set of features to use in identifying a substance, and an optimal pulse shape to use in order to enhance those features, the pulse shaper 400 is controlled by feedback via a genetic algorithm. The detector/analyzer 435 gathers scattered and fluorescent light from the sample. The gathered light may be separated into orthogonally polarized beams, and the spectrum of each beam is digitized and analyzed. Separately, the un-separated beams are passed through a pulse polarization phase shaper as illustrated in FIG. 7 and thence through a linear polarizer, and the phase delay of each spectral component is adjusted until a maximum amount of light is received at a detector 722. The relative phase of the two polarization components at each wavelength, and hence the polarization of each wavelength, may then be expressed for example in terms of the phase delays imposed at that wavelength by each of the two arms of the polarization pulse shaper. The complete configuration of a pulse can then be described in terms of the polarization, phase and amplitude of every spectral component of the pulse. These quantities may be arranged into a complex-valued matrix to represent the pulse. Both the stimulating pulse and the gathered light may be analyzed and represented using the same general matrix form.

A "satisfactory feature" may be defined as the difference between the two matrices describing gathered light when the sample is stimulated with two differently shaped pulses, when the correlation between the two matrixes is minimized by selecting different shapes for the two pulses. So, in the genetic algorithm controller, a fitness value is calculated as the correlation between the gathered light from two pulses separated by a time greater than the relaxation time of the sample. The shapes of the two pulses are controlled by the genetic algorithm, to search for two pulse shapes that produce maximally different stimulated signals from the sample.

The scanning near-field optical probe microscope of this embodiment may thereby be trained to recognize specific substances in a sample, with the high spatial resolution typical of scanning probe microscopes. If the microscope is trained to distinguish between individual nucleotides, it may be used to read directly the nucleotide sequence of a DNA molecule.

Embodiment #4: Molecular Scale Data Storage and Retrieval System

If a scanning probe microscope is used to selectively position different types of atoms or molecules at different locations on a surface 480 such as the surface of a silicon crystal or a quartz crystal, such that the arrangement of atom types encodes information, the scaning probe microscope of Embodiment #3 and FIG. 4 may be used to read the information. It is possible to manufacture replicas of such an arrangement of molecules in some cases. For example, if the original is in the form of various protein molecules bound to a surface, a replica may be made by pouring a mixture of antibodies to those protein molecules over the protein molecules. Complementary antibodies will bind to the protein molecules. A coating of silicone rubber, or a UV curable resin coating may then be applied over the antibody layer. After curing, the rubber or resin coating may be peeled off to make an intermaster. Finally, the process can be repeated using proteins or antibodies complementary to the antibodies first coated on the proteins, to make a replica of the original protein arrangement or an equivalent arrangement of antibodies on a resin or rubber surface. This process can be repeated multiple times, subject to the rate of degradation of the master or intermaster. This data storage and retrieval system potentially can store as much as ten terabytes per square centimeter.

Embodiment #5: Molecular Tags and a Reader for Secure Documents, Products or Packages In this embodiment, specific types of molecules are applied either randomly or in a pattern onto a label, tag or seal. The apparatus of Embodiment #1 or FIG. 4 may be used as a reader to determine the presence or absence of specific molecules, and the physical arrangement of specific molecules that are present, in order to judge the validity of the label, tag, or seal or to read information encoded in the selection and/or arrangement of the molecules. This system is analogous to a multicolor barcode system, in that selection of a molecule type is analogous to selection of an ink color, and the physical arrangement of molecule types is analogous to the physical arrangement of ink markings. In fact, this reader may be used to distinguish between different kinds of inks, or inks with different additives; in which case the analogy is closer.

Embodiment #6: CO2 Detector

Because the present methods provide a way to unambiguously detect the presence of any specific type of molecule, the apparatus of FIG. 12 may be used to detect the presence of carbon dioxide or any other potentially harmful gas or vapor in the air or in exhaust emissions. A sample of the air or other gas or vapor to be tested is passed through the tube 1265, or equivalently through an unconfined optical path. A measurement of the quantity or concentration of a specific substance in a sample may be obtained by comparing the intensity of the emitted fluorescent signal to the intensity of the stimulating pulse, at the optimum pulse shape. To obtain a stronger signal by in creasing the path length through the sample volume, the optical path may be folded using mirrors. When the path length over which the shaped pulse interacts with the sample is very long, it is advantageous for the detector 1237 to observe selected features in the absorption spectrum and optimize the pulse shape to enhance those selected features.

Embodiment #7: Cell Sorter

Figure 13:
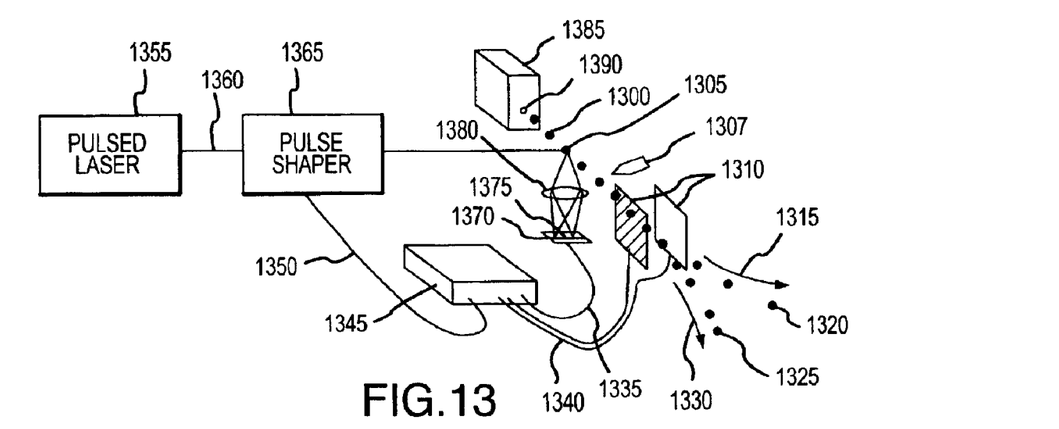
FIG. 13 illustrates an apparatus for sorting particles via shaped pulse identification
Figure 14A:
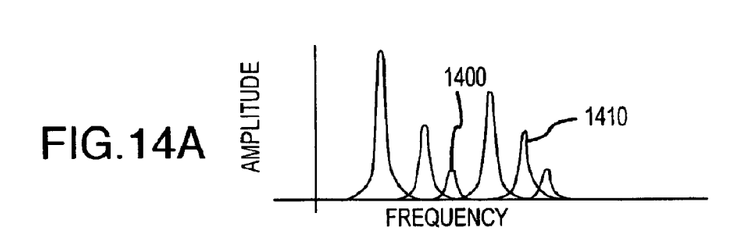
FIG. 14 is an illustration of enhancement of a complex spectral feature by shaped pulse excitation. Part A represents the spectral response of a substance to an unstructured white-light pulse; Part B represents the spectral response of the same substance to an optimally shaped pulse, and Part C represents the difference between normalized versions of the two spectra.
Figure 14B:
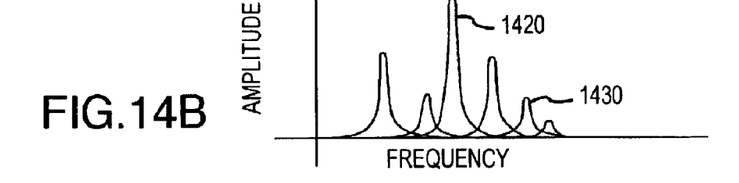
Figure 14C:
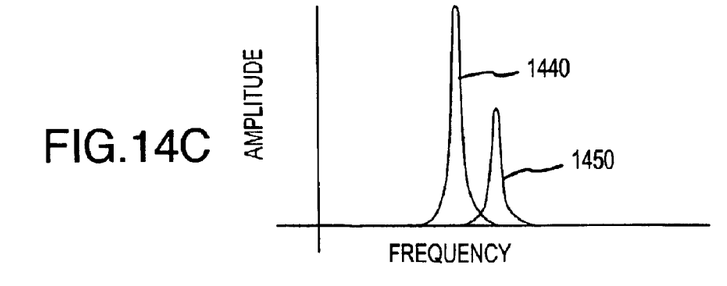

The apparatus of FIG. 13 is capable of detecting and identifying specific kinds of microbes and spores, and it may be used as a cell sorter. A droplet (e.g., 1300) diluted sufficiently that it probably contains a single cell or spore of the type of interest is formed and moved through a focal region 1305. An ink jet printer head 1385, for example, can form and launch droplets of very consistent small size at a high rate. A pulse (from a pulsed laser 1355) shaped by a pulse shaper 1365 to selectively stimulate a specific type of cell or spore illuminates each droplet, and light scattered and emitted by the droplet is gathered by optics 1380, directed onto detector 1370 and analyzed by computer 1345. If desired, filters may be positioned anywhere between focal point 1305 and the detector 1370 to pass only selected parts of the spectrum to the detector; however, if the optical system 1380 employs a prism or diffractive element to spread the spectrum of the light from the sample onto a detector array 1370, it is not necessary to filter the spectrum optically. The computer 1345 may employ an FPGA or other highly parallel signal processor for high speed, or it may be a high speed serial computer. The droplet 1300 may then be charged by ion source 1307 or electron source 1307 and deflected electrostatically by voltages applied to plates 1310 or by gas jets or other deflection means 1310 under the control of computer 1345 into different paths 1315, 1330 according to whether or not a specific type of microbe or spore has been detected in the droplet. This system has applications in directed evolution of microbes, medical diagnostics, and assays of microbial populations.

Embodiment #8: Optical Security Device

An optical security device can be made by applying specific nonlinear optical materials such as fluorescent dyes or specific proteins to a tag or label. In FIG. 4, such a label 480 bears stripes of inks containing fluorescent quantum dots such as ZnSe-capped CdS nanocrystals. Alternatively, markings or taggants 463 may be applied to a surface 480 of a product in the form of a pattern of nonlinear and linear optical materials in a resonant structure such as a multilayered interference filter, or particles of nonlinear optical materials may be incorporated into the volume of the label or surface 480. An appropriately tailored optical pulse illuminating a spot 470 will move the fluorescent particles or nonlinear optical materials or structures into an excited state, which will decay by emitting light and/or phonons. The emitted spectrum or absorption spectrum may be detected and analyzed by detectors 435 and computer 425, to identify the markings, materials, particles, patterns or structures and thereby determine the identity or validity of tag, label, document or product 475.

Embodiment #9: Opto-acoustic Signals Stimulated by Shaped Optical Pulses

Figure 10:
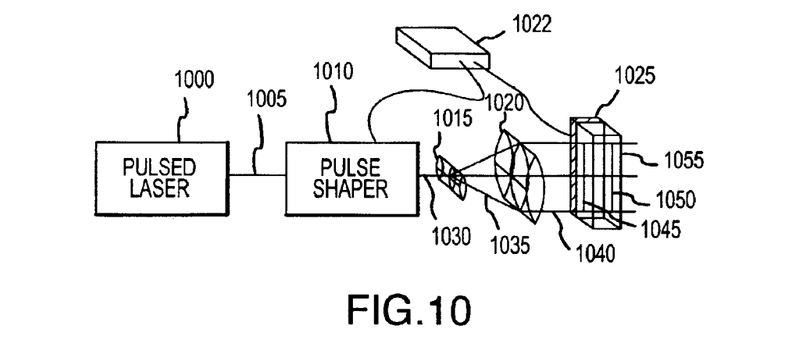
FIG. 10 illustrates an opto-Acoustic apparatus including a cuvette, an acoustic transducer, optics to form a thin "sheet" of light, a pulsed laser and a pulse shaper. The pulse shaper can include the ability to shape the polarization of the pulse.

Molecules of a given type in solution will emit a characteristic acoustic pulse when stimulated by an optical pulse. The detailed shape of the acoustic pulse depends on the optical spectrum of the molecules and the details of energy exchange between the molecules in their various states and the surrounding medium. Thus, an optical pulse having the specific shape to place the molecules into a specific excited state will cause the molecules to emit an acoustic pulse having a distinctive shape. In FIG. 10, a shaped optical pulse excites a target molecule type in a cuvette 1055. Acoustic energy emitted by the molecules in response to the pulse is picked up by acoustic transducer 1025 and analyzed by computer 1022.

Embodiment #11: Improved Scanned Probe Near-field Optical Microscope

The response of a molecule to an optical pulse depends on the polarization of the pulse, the orientation of the molecule, the quantum state of the molecule and the atoms composing the molecule, and the phase of the quantum state. Accordingly, it is advantageous to precondition the molecules so that a large fraction of the molecules in a sample are aligned and in a specific quantum state and phase. This preconditioning may be obtained by several methods. One method is to use a relatively long optical pulse tailored in frequency and polarization to align nuclei in the molecules, for example via the Overhauser effect. Another method is to place the sample in a stationary magnetic field modulated by a rotating magnetic field as is standard in NMR technology, to align the molecules or nuclei and synchronize their precessional phases. Another method is to mechanically align molecules by embedding them in a stretchable material and stretching the material. Yet another method is to crystallize the molecules or incorporate them in a crystalline matrix composed of another material.

Figure 8:
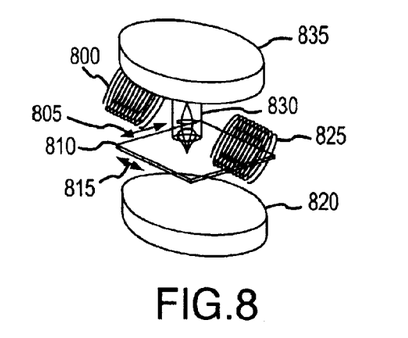
FIG. 8 illustrates an apparatus including a strong static magnet, RF coils, and a near-field probe for combining NMR spectroscopy and scanned optical near-field microscopy with tailored-pulse excitation.

The scanning near-field optical microscope of FIG. 4 may be modified as in FIG. 8 to further enhance the signal from a sample. FIG. 8 illustrates the optical head of FIG. 4, with field magnet poles 820 835 added, and RF coils 800 825 added. The quantum state of the target molecules or atoms in a sample on substrate 805 may be preconditioned using the magnetic field generated by poles 820 835 and the RF coils 800 825 or by the optical Overhauser effect using a preconditioning light pulse of specific frequency and polarization. The pre-conditioned sample may then be probed using one or more further pulses shaped optimally to enhance features in the optical absorption or emission spectrum of the sample. Alternatively or in addition, RF signals picked up by coils 800 825 may be analyzed to provide information further useful in identifying and detecting the target molecules or atoms in the sample using standard NMR techniques.

All of the embodiments described above may additionally include means to generate multiple coherent pulses with adjustable delays between pulses. FIG. 7 illustrates one such means. An original pulse with, say, a Gaussian shape, is converted to several coherent pulses of nominally identical shape using a train of beamsplitters 700, 770, 760. Additional elements 750, 765 may be inserted in the beam paths to ensure that all pulses experience the same dispersion. Pulse shapers 710, 745, 740 may be inserted in the paths to shape each pulse independently, and then the pulses may be directed into a common beam path using beamsplitters 715, 725, 730. Coherent pulse amplifiers 721 may be inserted into the separate paths or into the common beam path, and attenuators 780, 785 may be inserted to control the relative amplitudes of the different component pulses. By adjusting the length of each path (for example by moving the mirrors 750), the timing between pulses may be adjusted. Multiple, mutually coherent, independently shaped pulses are advantageous because they may be used to prepare a desired quantum state of a molecule and then probe the state. For example, the absorption spectrum of a molecule depends on the state it is in. The first pulse can drive the molecule into a given state, and the absorption spectrum of the molecule relative to the second pulse is then distinctive of the molecule in that state. Furthermore, the absorption cross section of a photon by a molecule depends on the polarization, wavelength and phase of the photon as well as the quantum state of the molecule, so the absorption spectrum measured via the second pulse may depend strongly on the detailed shape of the pulse.

Note that the superposition of two coherent light beams of orthogonal polarization and having slightly different wavelengths results in a rotating electric field vector and a rotating magnetic field vector in the light beams, rotating at a frequency dependent on the frequency difference between the two beams.

Specific elements and combinations of elements of the embodiments and techniques described herein may be changed without departing from the scope of the invention as long as the essential principles are followed. For example, microwave radiation or acoustic radiation may be substituted for light radiation if the pulse shaper is of a type suitable for shaping microwave or acoustic pulses respectively. Fiber optic beamsplitters instead of cube beamsplitters may be used for splitting and combining pulses. A polarization pulse shaper may act upon any orthogonal polarization components of a pulse such as orthogonal linear polarizations, orthogonal circular polarizations or orthogonal elliptical polarizations. The pulses may be of any suitable duration including femtoseconds, picoseconds, nanoseconds, microseconds or milliseconds depending on the quantum state structure of the target particles or substances.

The shaped pulses made by the polarization pulse shaper may be used in any application in which it is beneficial to tailor the polarization shape as well as the phase and amplitude shape of a pulse, such as in controlling chemical reactions, separating isotopes, inducing optical transparency, preparing specific quantum states for a quantum computer, or enhancing the ability of a light pulse to damage a target.

The term, "substance" as used herein, means particles, cells, spores, molecules, atoms, crystalline structures, quantum dots, or nanocrystals having consistent optical properties and emission or absorption spectra that depend on the shape of a stimulating coherent radiation pulse. The term, "particle" is used to refer to any object smaller than approximately 50 microns in diameter, including cells, spores, pellets. The particles may themselves be composed of substances that are detected or recognized by the apparatus as described herein, or they may be tagged or marked with such substances.

What is claimed:

1. Apparatus for detecting the presence of specific target substances in a sample, comprising:

a source of coherent radiation pulses of consistent initial shape and duration;

a pulse shaper capable of independently controlling a combination of phase, amplitude and polarization of a plurality of the spectral components of said radiation pulses according to a set of control parameters and thereby controlling the shape of the pulses to form re-shaped pulses;

system controller means for imposing sets of pulse shaper control parameters based on the specific target substance;

means for directing the re-shaped pulses to the sample; and means for measuring the difference between the spectrum of radiation emitted or absorbed by the sample in response to a first re-shaped pulse and the spectrum of radiation emitted or absorbed by the sample in response to a second re-shaped pulse, the control parameters for said first re-shaped pulse and said second re-shaped pulse being selected to provide a significant difference between the response spectra of the target substance and the response spectra of likely background or contaminant substances.

2. The apparatus of claim 1 wherein said system controller includes a library of control parameter sets, each set optimized for a corresponding target substance.

3. The apparatus of claim 1 wherein said source of coherent radiation pulses comprises a femtosecond pulsed laser.

4. The apparatus of claim 1 wherein said means for directing the re-shaped pulses to the sample comprises:

a sample holder; and optical elements to convey the pulses to the sample on the sample holder.

5. The apparatus of claim 1, further comprising:

magnetic field generating means to impose a static magnetic field on the specimen;

RF coils and means for driving current through said RF coils at frequencies that correspond to characteristic frequencies of the target substance; and means for measuring changes in the electrical current through said RF coils.

6. The apparatus of claim 1, further comprising means for generating a plurality of said re-shaped pulses with predetermined delays between the pulses;

means for measuring the emission or absorption spectrum of the sample resulting from each of the pulses, and means for comparing the emission or absorption spectra resulting the different pulses at different times.

7. A particle sorter comprising:

the apparatus of claim 1 for detecting and identifying specific substances;

means for passing small volumes of a fluid through a region illuminated by the shaped pulses of claim 1; and means for directing the small volumes of fluid into different paths according to the spectral response of each small volume.

8. A security mark reader comprising:

the apparatus of claim 1;

means for positioning in the path of said re-shaped pulses a document or product bearing a mark containing information in the form of distinct combinations of a plurality of different substances in different regions of said mark; and means for determining the information content of said mark based on the emission or absorption spectra of the different regions of said mark in said regions of said mark.

9. Apparatus for detecting the presence of specific target substances in a liquid or solid sample, comprising:

a source of coherent radiation pulses of consistent initial shape and duration;

a pulse shaper capable of independently controlling a combination of phase, amplitude and polarization of a plurality of the spectral components of said radiation pulses according to a set of control parameters and thereby controlling the shape of the pulses to form re-shaped pulses;

system controller means for imposing sets of pulse shaper control parameters based on the specific target substance;

means for directing the re-shaped pulses to the sample; and means for measuring the difference between the time-dependent spectrum of acoustic radiation emitted or absorbed by the sample in response to a first re-shaped pulse and the spectrum of radiation emitted or absorbed by the sample in response to a second re-shaped pulse, the control parameters for said first re-shaped pulse and said second re-shaped pulse being selected to provide a significant difference between the response spectra of the target substance and the response spectra of likely background or contaminant substances.

10. A selective particle modifier comprising:

a source of consistently shaped initial pulses of coherent, broad-spectrum radiation;

means for re-shaping the initial pulses with respect to a combination of polarization, phase and amplitude, the shapes of said pulses optimized to induce chemical or physical changes in a target substance through manipulation of specific quantum states in said target substance, said chemical or physical changes serving to modify or trigger the modification of the particle;

means for directing the re-shaped pulses onto material containing some particles that contain said target substance, so that the re-shaped pulses cause modification of primarily those particles containing the target substance.

11. The particle modifier of claim 10, wherein said chemical or physical changes causes the destruction, denaturization, or inactivation of said particles.

12. A detector and identifier of airborne particles, said detector comprising:

a source of coherent radiation pulses of consistent initial shape and duration;

a pulse shaper capable of independently controlling a combination of phase, amplitude and polarization of a plurality of the spectral components of said radiation pulses according to a set of control parameters and thereby controlling the shape of the pulses to form re-shaped pulses;

system controller means for imposing sets of pulse shaper control parameters based on a specific target substance;

means for directing the re-shaped pulses through the air over a predetermined path; and means for measuring the difference between the spectrum of radiation absorbed along the path in response to a first re-shaped pulse and the spectrum of radiation absorbed along the path in response to a second re-shaped pulse, the control parameters for said first re-shaped pulse and said second re-shaped pulse selected to provide a significant difference between the response spectra of the target substance and the response spectra of likely background or contaminant substances.

* * * * *